(12) United States Patent
Vassarotti

(10) Patent No.: US 6,375,855 B1
(45) Date of Patent: Apr. 23, 2002

(54) METHOD, DEVICE AND APPARATUS FOR CONCENTRATING AND/OR PURIFYING MACROMOLECULES IN A SOLUTION

(75) Inventor: Vincenzo Vassarotti, Bugnaux sur Rolle (CH)

(73) Assignee: Vivascience, AG, Hannover (DE)

( * ) Notice: Subject to any disclaimer, the term of this patent is extended or adjusted under 35 U.S.C. 154(b) by 0 days.

(21) Appl. No.: 09/101,749

(22) PCT Filed: Dec. 2, 1997

(86) PCT No.: PCT/EP97/06953

§ 371 Date: Jul. 15, 1998

§ 102(e) Date: Jul. 15, 1998

(87) PCT Pub. No.: WO98/26859

PCT Pub. Date: Jun. 25, 1998

(30) Foreign Application Priority Data

Dec. 2, 1996 (SE) ............................... 9604441

(51) Int. Cl.[7] ........................ B01D 21/26; B01D 33/15; B01D 24/32; G01N 9/30; G01N 35/00
(52) U.S. Cl. .................... 210/787; 210/781; 210/360.1; 210/361; 422/72; 422/101; 422/102; 436/45
(58) Field of Search .............................. 494/16, 36, 37; 422/72, 101, 102; 436/177, 45; 210/781, 360.1, 787, 361, 406, 416.1; 159/6.1

(56) References Cited

U.S. PATENT DOCUMENTS

| | | | | |
|---|---|---|---|---|
| 3,583,627 A | * | 6/1971 | Wilson | |
| 4,872,988 A | * | 10/1989 | Culkin | |
| 4,948,564 A | * | 8/1990 | Root et al. | 422/101 |
| 5,888,831 A | * | 3/1999 | Gautsch | 422/101 |
| 6,103,195 A | * | 8/2000 | Shukla et al. | 422/70 |
| 6,156,199 A | * | 12/2000 | Zuk, Jr. | 210/321.84 |
| 6,221,655 B1 | * | 4/2001 | Fung | 435/288.1 |
| 6,225,130 B1 | * | 5/2001 | Kitajima et al. | 436/177 |

FOREIGN PATENT DOCUMENTS

| | | | |
|---|---|---|---|
| DE | 33 42 703 | * | 5/1984 |
| EP | 0 338 844 | * | 10/1989 |
| EP | 0 718 618 A2 | * | 6/1996 |
| GB | 2 290 244 | * | 12/1995 |
| WO | WO 94/27724 | * | 12/1994 |

* cited by examiner

Primary Examiner—Jill Warden
Assistant Examiner—Brian R Gordon
(74) Attorney, Agent, or Firm—Young & Thompson

(57) ABSTRACT

A device for concentrating and/or purifying macromolecules in a solution has a concentration chamber (1) with a sample reservoir (2) for a liquid sample to be processed, a filter (3) for filtering the liquid sample, and a filtrate container (4) for collecting the filtrate. A gas pressure differential is created and maintained across the filter and a sealing cap (5) for the sample reservoir (2), which has an opening (6) for permitting gas flow in one direction and blocking aerosol or liquid flow in an opposed direction. The present invention also provides apparatus and methods employing the device.

21 Claims, 7 Drawing Sheets

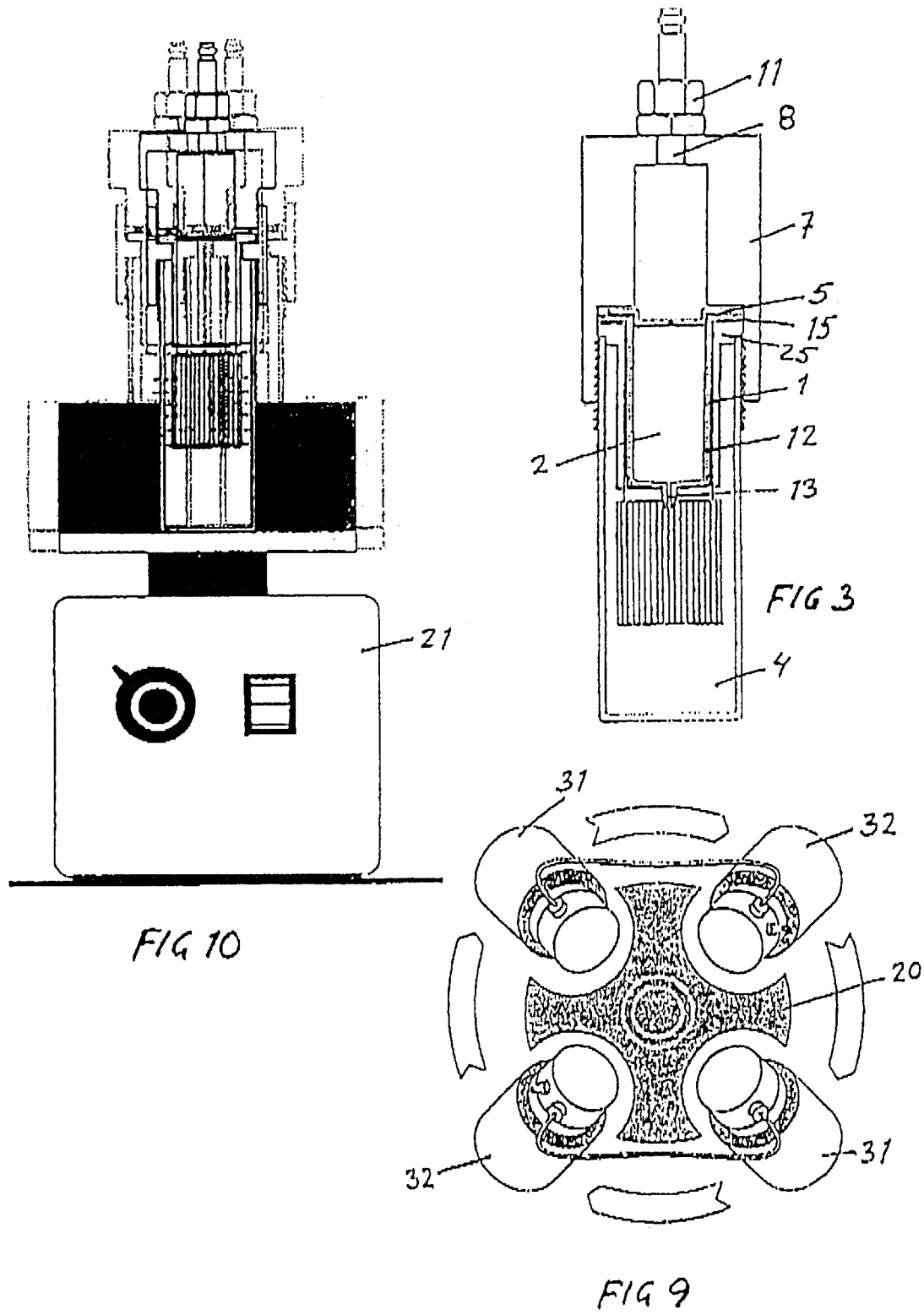

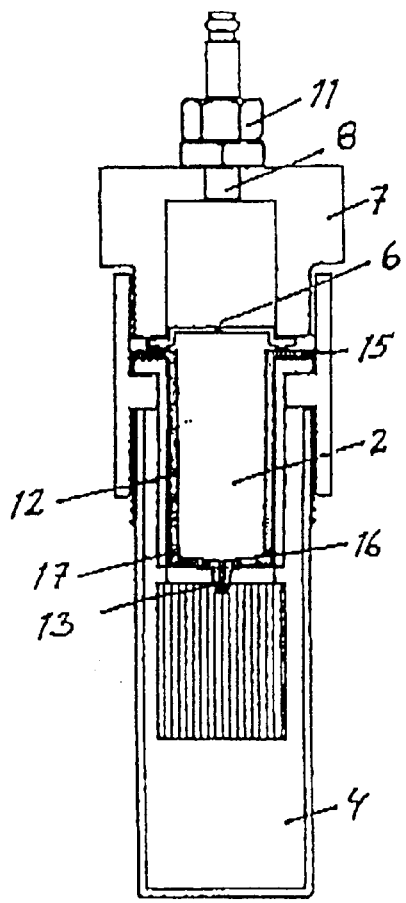
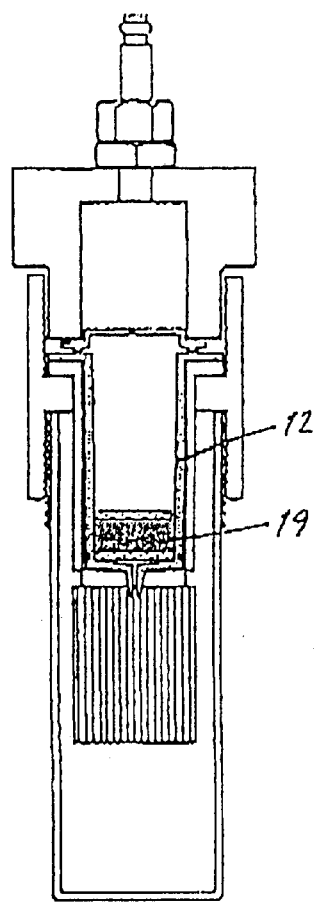
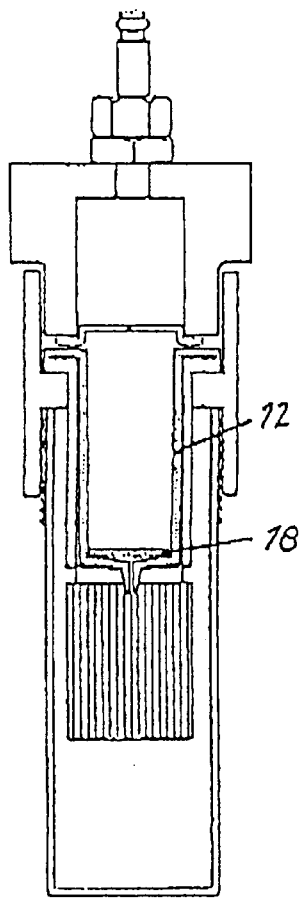
FIG 4A  FIG 6A  FIG 5A
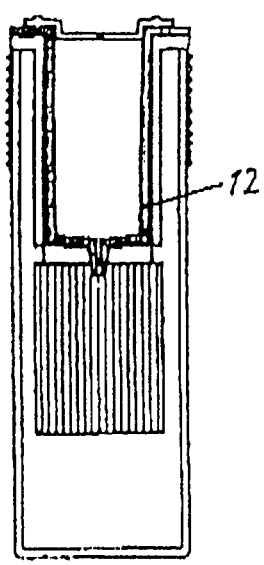
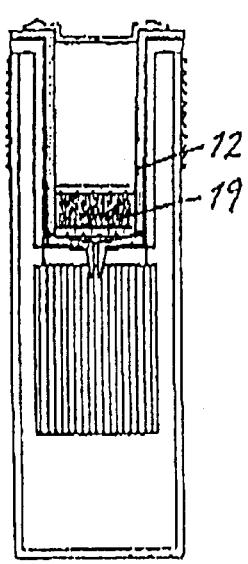
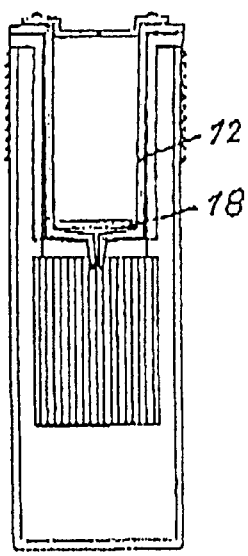
FIG 4B  FIG 6B  FIG 5B

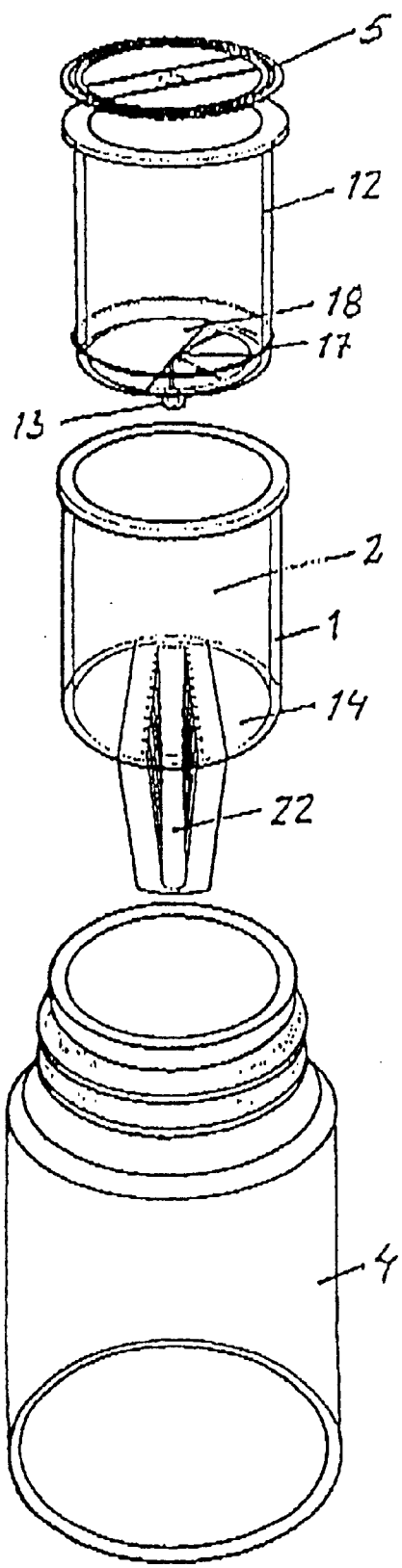
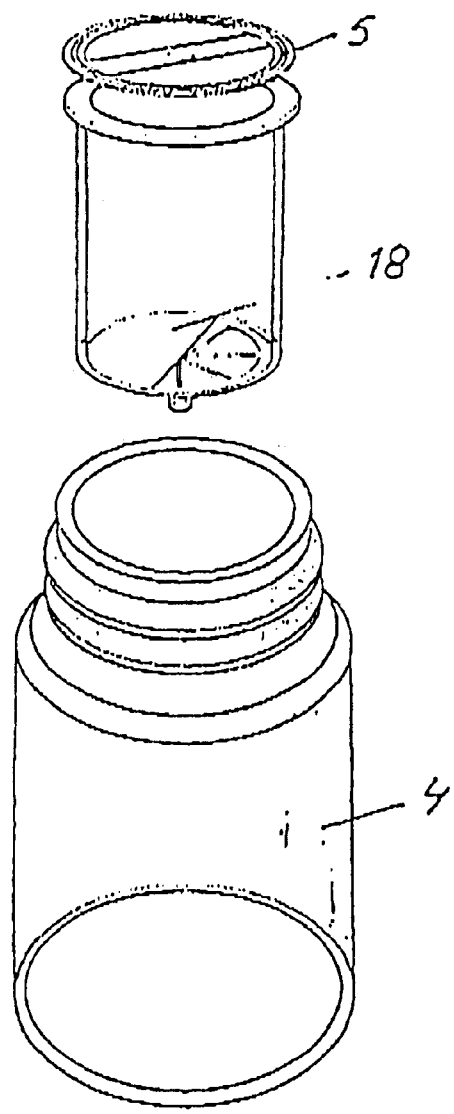
FIG 7A
FIG 7B

METHOD, DEVICE AND APPARATUS FOR CONCENTRATING AND/OR PURIFYING MACROMOLECULES IN A SOLUTION

TECHNICAL FIELD

This invention relates to modular devices and methods for concentrating and/or purifying macromolecules in a solution as well as apparatuses including such devices.

The basic device comprises essentially a pressure resistant concentration chamber which can be provided with modular accessories adapting the device for use with a choice of gas pressure, vacuum, centrifugal forces or a combination of gas pressure and centrifugal forces.

The pressure resistant concentration device can be used either in a centrifuge, on a laboratory agitator or as a free standing pressurised or vacuum driven filtration cell. Interchangeable accessory-modules makes it possible to process the solution by means of e.g. two stage filtration, a combined diafiltration and concentration procedure or by means of one or more solid phase extraction steps which can be carried out in combination with sample concentration.

BACKGROUND ART

Many biotechnology laboratories use micro- and ultrafiltration methods in the processing of biological solutions. As examples, filtration is used as a sterilising step to remove bacteria, as a clarification step to remove suspended solids and contaminants, as a concentration step for proteins and other macromolecules or as a purification step to eliminate unwanted micromolecules such as salts. Alternative membranes and porosities are used to suit specific applications and process requirements.

Filter elements are mounted in a broad array of holders and forces due to liquid or gas pressure, vacuum or centrifugal forces are used to transport the filtrate through the filter element. This results in a very broad offer of products to the research scientist who must invest in many alternative products and processing techniques to cover a broad range of filtration requirements.

Amongst the more popular techniques for filtration of laboratory biological samples are centrifugal-force-techniques and a technique making use of gas pressurised cells. For single samples, stirred cells are more popular whilst multiple samples are more frequently processed in centrifuges where more than one sample is usually required to balance the centrifuge. As up until now, the filter holders have been incompatible for use in both a stirred cell and centrifuge, laboratories have had to purchase both types of filter holders to fully cover their requirements.

Pressurised cells frequently use a stirring bar mechanism to maintain the solution being processed in suspension and in order to inhibit the build-up of macromolecules on the membrane surface which would result in reduced filtration speed. Whilst stirring mechanisms are quite effective for this purpose, they also induce shear forces which can denature macromolecules and reduce the biological activity of the solution.

In order to clear a higher proportion of contaminating micromolecules during the filtration process, an additional container could be linked by a tube to the filtration cell feeding a buffer solution to the filtration cell at the same speed as effective filtration. The filtrate is carried by another tube to another adjacent container. Several tubing connections and a large amount of bench space is required to accommodate the various containers.

In centrifugal filtration procedures, during the first stages of filtration, pressure across the membrane is high due to the high centrifugal force on the full initial volume of the sample and filtration speed is therefore at its peak. However, as filtration progresses and the solute above the membrane is reduced, filtration speed is also reduced and achieving a high level of filtration becomes very time consuming. Whilst a proportional increase in centrifugal speed can theoretically maintain a constant trans-membrane pressure that is usually not possible due to limitations in the maximum speed of centrifuges and the mechanical limitations of the filter holder.

Another problem with centrifugal ultrafiltration is that the concentration device cannot be sealed from the outside environment as an air passage is necessary at the head of the device to stop generating retentive vacuum as filtration progresses. This can cause the build up of aerosols during the centrifugation process and contamination of the centrifuge itself. This is a particular problem with toxic and dangerous substances. Whilst protective containers for the whole filtration assembly are sometimes used, these are expensive and reduce the capacity of the centrifuge rotor.

In order to reduce the number of filtration steps required in sample processing, some device holders can be stacked together to provide a double filtration during the centrifugal process. For example, a solution may pass through a first relatively coarse filter for clarification followed by the concentration of the molecules of interest by retaining them in an impermeable area on the edge of the second filter. The objective is to clear a maximum of the solute of interest through a relatively coarse first filter which is ideally positioned at 90° to the vector force and then avoid the build up of the solute on the second tighter filter by positioning the second membrane element at an angle to the vector force. Up until now this technique has been limited by the fact that the surfaces of stacked filters have been arranged in parallel to each other.

In addition to filtration, chromatography techniques e.g. making use of solid phase extraction columns are sometimes used to complement filtration and achieve a higher level of sample purification. This is normally a separate step to filtration in the processing of biological samples and is therefore time consuming. Also, solid phase extraction columns are difficult to control as solution flow through the gel bed must be sufficiently slow to allow target molecules to be fully captured by the sorbent bed. In most cases this precludes the use of gas pressure or centrifugation because of excessive flow rates through the sorbent material. More common techniques such as the use of a manually controlled syringe is time consuming and often inconsistent; or alternative the use of vacuum filtration manifolds require additional capital investment and longer set up times.

BRIEF DESCRIPTION OF THE INVENTION

One object of this invention is to provide a filtration cell or device which can be used in either a centrifuge or as a pressure driven free standing unit thereby eliminating the need for specific single and multiple sample filtration devices.

It is another object of this invention to provide a pressure driven filtration cell or device which eliminates the need for a stirring mechanism for the purpose of creating turbulence, sample agitation being provided by an external shaking or vortex inducing action.

It is another object of this invention to provide a pressure driven filtration cell or device which requires reduced bench space and eliminates the need for tube connections to ancillary containers when the device is used in e.g. a diafiltration procedure.

It is another object of this invention to provide a pressure driven filtration cell or device which can be used in either a centrifuge or as a pressure driven free standing unit, which when used under gas pressure in a centrifuge, combines the filtrate driving forces from gas pressure and gravity for improved flexibility and control of the filtration procedure.

It is another object of this invention to provide a pressure driven filtration cell or device which can be used in either a centrifuge or as a pressure driven free standing unit, which when used under gas pressure e.g. in a centrifuge eliminates the need for an air passage between the sampler reservoir and the external environment.

It is another object of this invention to provide a pressure driven filtration cell or device which can be used in either a centrifuge or as a pressure driven free standing unit which comprises two membrane elements and in which the proportion of solvent to be retained by each filter element can be controlled.

It is another object of this invention to provide a pressure driven filtration cell or device which can be used in either a centrifuge or as a pressure driven free standing unit, which in addition to a filtration step can provide a solid phase extraction step whereby the speed of flow across the sorbent in the extraction step is controlled by the back pressure generated by the membrane element.

It is another object of this invention to provide a pressure driven filtration cell or device which can be used in either a centrifuge or as a pressure driven free standing unit, which has an integrated reservoir which feeds a washing solution at the same rate as contaminants are cleared through the filtration membrane. It is further an object of this invention to provide a modular device which alternatively can be set up and used in pressurised and non-pressurised mode.

It is also an object of this invention to provide new apparatuses including devices according to the invention in pressurised or non-pressurised mode.

It is further an object of this invention to provide new methods for processing liquid samples making use of devices or apparatuses according to the invention.

BRIEF DESCRIPTION OF THE DRAWINGS

Further objects, uses and advantages with the invention will be apparent from the reading of this description which proceeds with reference to the accompanying drawings forming part thereof and wherein:

FIG. 3 shows a further embodiment of the device according to the invention.

FIG. 4A shows a basic device for operation under pressure according to the invention additionally provided with a diafiltration insert reservoir.

FIG. 4B shows a device according to the invention for operation without over-pressure provided with a diafiltration insert reservoir.

FIG. 5A shows a basic device for operation under pressure according to the invention additionally provided with a secondary filtration insert reservoir.

FIG. 5B shows a device according to the invention for operation without over-pressure provided with a secondary filtration insert reservoir.

FIG. 6A shows a basic device for operation under pressure according to the invention additionally provided with an insert reservoir containing a gel bed.

FIG. 6B shows a device according to the invention for operation without over-pressure provided with an insert reservoir containing a gel bed.

FIG. 7A shows a device according to the invention in perspective for operation without overpressure provided with a secondary filtration insert reservoir.

FIG. 7B shows a device according to the invention in perspective for operation without overpressure provided with a filtration insert reservoir.

FIG. 9 shows the principal arrangement of two pressurised devices according to the invention in a centrifuge and two auxiliary communicating pressure vessels.

FIG. 10 shows a device according to the invention arranged on an agitation apparatus.

DETAILED DESCRIPTION OF THE INVENTION

Basic filter device

Figure 1:
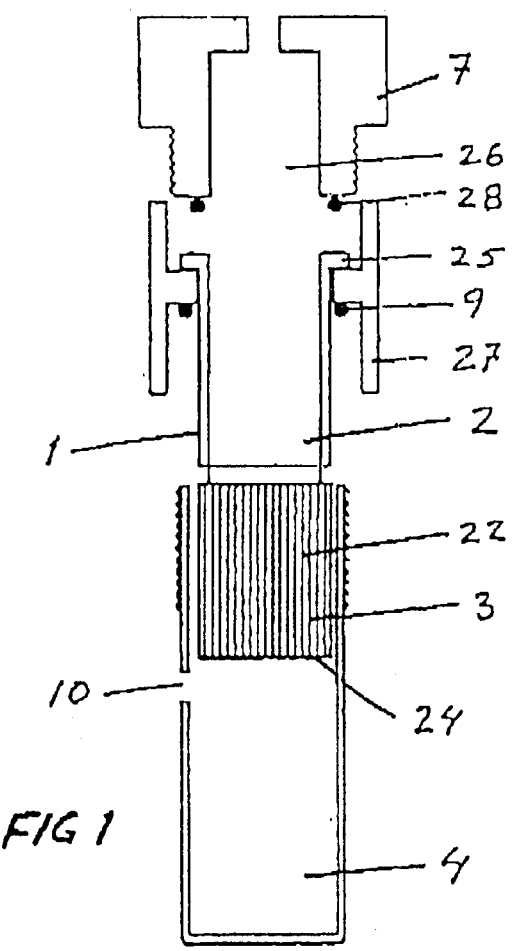
FIG. 1 schematically shows different parts forming an embodiment of the device according to the invention.
Figure 8:
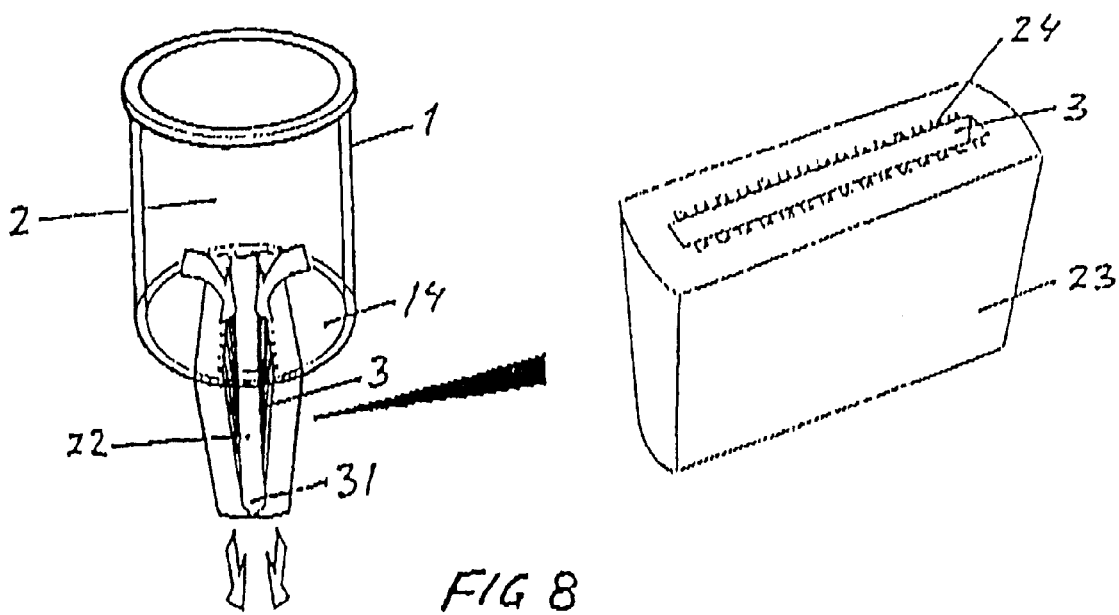
FIG. 8 shows a part of a device according to the invention in perspective and a section through the sleeve surrounding the filtration chamber.

FIG. 1 shows a number of parts forming an embodiment of the device according to the invention. A concentration chamber 1 comprises a cylindrical sample reservoir 2 arranged to receive the sample to be processed. The concentration chamber is provided with one or more filtration membranes 3 fitted at the bottom portion or in the sidewall of said chamber below said sample reservoir. In the following description a concentration chamber, cf. for instance FIG. 8, is referred to in which a thin, slightly tapered filtration chamber 22 communicating with the sample reservoir 2 is arranged below the sample reservoir having a volume which is only a small fraction of the total volume of the concentration chamber, e.g. less than 15%. In the embodiment shown two opposite flat sidewall portions of the filtration chamber 22 carries two filtration membranes 3 for fast filtration which are fixed and supported against apertures in said sidewalls by means of an external sleeve 23 having longitudinal filtrate ducts 24 on the inside minimising the hold up volume. The vertical lines on the filtration chamber 22 in e.g. FIG. 1 illustrate these ducts. At the lower portion of the filtration chamber an impermeable dead stop pocket 31 prevents concentration to dryness. This type of concentration chamber which has proven to be very efficient is known as such from the European Patent Application EP94916988.2. The concentration chamber is arranged in a cylindrical filtrate container 4 and is positioned at a suitable height from the bottom of the filtrate container so as to leave sufficient space for the filtrate to collect below the membranes. An external flange 25 around the upper portion of the concentration chamber resting against e.g. the opening of the filtrate container has proven to be most appropriate arrangement for this purpose but any other fixation arrangement such as a screw thread or interference fit may be used to position the concentration chamber away from the bottom of the filtrate container 4.

A pressure resistant head portion 7 could be fixed on top of the concentration chamber. This head portion 7 could be provided with a chamber 25 for compressed air or gas. In the embodiment according to FIG. 1 the head portion 7 is fixed against the concentration chamber by means of a threaded connection ring 27 which normally first is screwed on to the filtrate container and thereafter receives the concentration chamber and the head portion. The head portion 7 has an inlet 8 for compressed gas or air which can be provided with a check valve.

FIG. 1 also schematically shows an outlet 10 for evacuating gas or air from the filtrate container. In order to create a gas pressure related pressure difference across the filter means 3 it is thus possible to either evacuate the filtrate container or pressurize the sample reservoir. Suitable sealing arrangements 9 and 28 which could be ordinary O-rings are also shown. In certain embodiments an additional sealing under the flange 25 could also be suitable.

Figure 2:
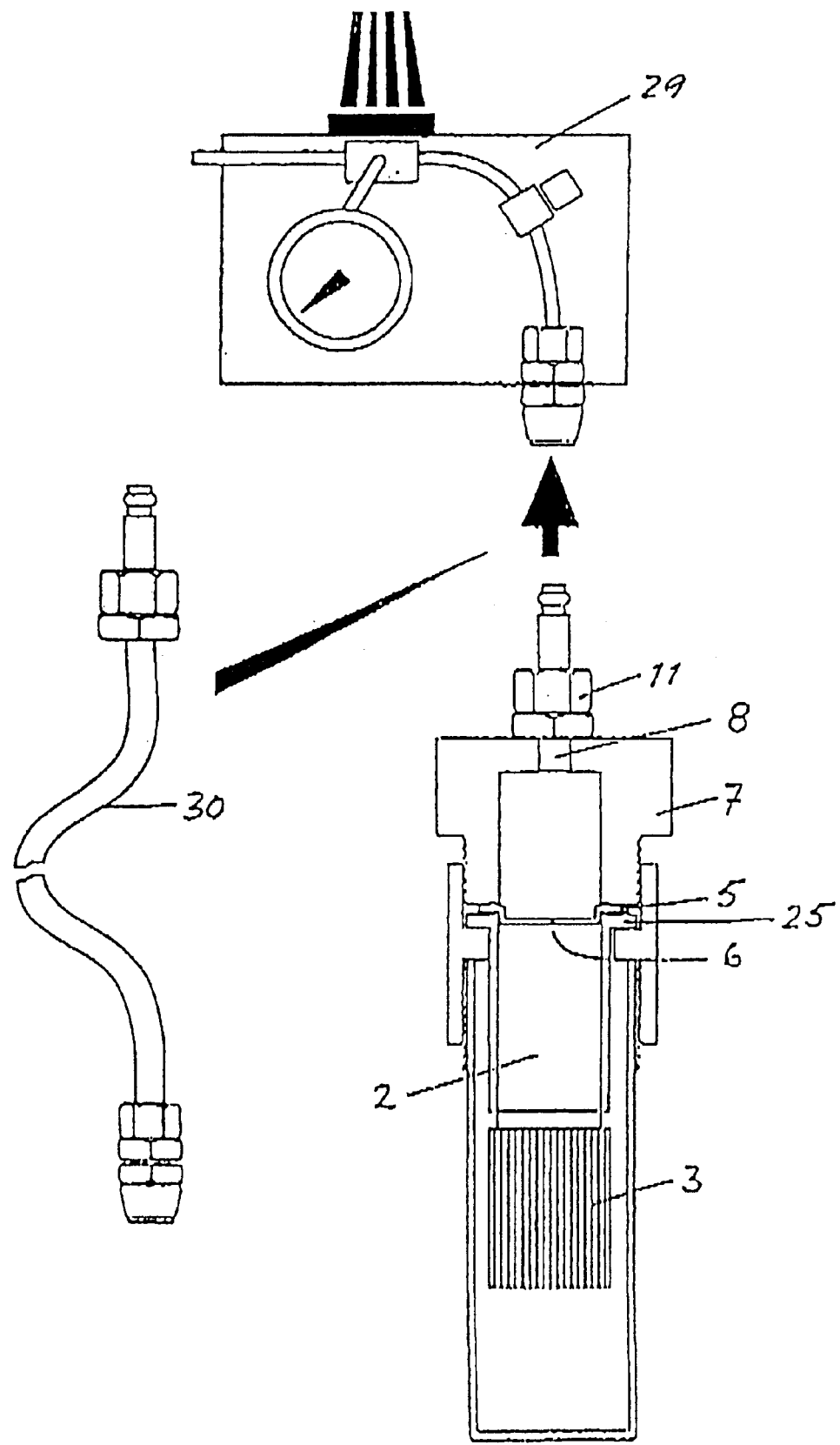
FIG. 2 shows parts according to FIG. 1 assembled to a device according to the invention and an external pressure source used to pressurize the device.

In FIG. 2 an assembled embodiment of a device according to the invention is shown. A sealing cap 5 having a general U-formed section and which is preferably made of elastomeric material is used to seal the concentration chamber 1. The cap is preferably provided with an integrated O-ring type seal on its periphery which gives a good sealing effect between the head portion 7 and the flange 25 on the concentration chamber 1. Additionally, the cap is provided with at least one small hole or slit 6 to allow air to pass between the chamber 26 and the sample reservoir at the same time as it is blocking splashing liquid in the opposite direction. In this embodiment air or gas escapes from the filtrate container during the filtration process through the passage defined by the lower threaded portion of the connection ring and/or the passage defined by the underside of the flange 25 and the upper threaded portion of the connection ring.

The device according to this figure can be connected to an external source for pressurised air or gas 29. If the device is provided with a check valve 11 at the inlet 8 the device can be disconnected after it has been pressurised. In certain applications especially when a larger volume of compressed gas is needed the device can be kept connected to the source 29 by means of a tube connection 30 during the filtration process.

From FIG. 2 it is, however, clear that the assembly of the device could be made in another order than described in connection with FIG. 1. The concentration chamber 2 with the sample to be processed provided with the combined cap and sealing 5 can e.g. first be put into the connection ring 27. Then the head portion 7 is screwed into the ring 27. In principle such a partly assembled device could then be pressurised before it is finally screwed onto the filtrate container 4. If for some reason, e.g. a too high pressure (normal pressures in the context is 4–10 bars) or a defect concentration chamber the latter should break or even explode before it is mounted in the surrounding filtrate container this could of course be annoying or even dangerous. Fragments of the concentration chamber could cause injuries and the sample to be processed could be toxic or otherwise dangerous. Thus there is risk that an inexperienced user could create some damages.

Another embodiment of the device is shown in FIG. 3. The connection ring 27 has been eliminated and the head portion 7 is fixed directly on to the filtrate container 4. The concentration chamber 1 can have a diameter so that it fits into the filtrate container 4 without or with very small lateral play. In the alternative the flange 25 can have a lower portion with a diameter which equals the inner diameter of the filtrate container.

An advantage with this device is that it can not be pressurised before it is completely assembled, i.e. the concentration chamber is positioned inside the filtrate container. Thus, if the concentration chamber breaks for some reason the filtrate container will protect the environment.

This embodiment also shows an insert reservoir 12 inserted into the sample reservoir 2. This arrangement will be described more in detail below but it could be noted already now that if the device should be used without insert reservoir the sealing cap 5 could easily be inverted and fixed into the head portion 7 to keep it centered in the device because the diameter of the cylindrical gas/air chamber 26 is the same as the inside diameter of the insert reservoir 12.

Figure 11:
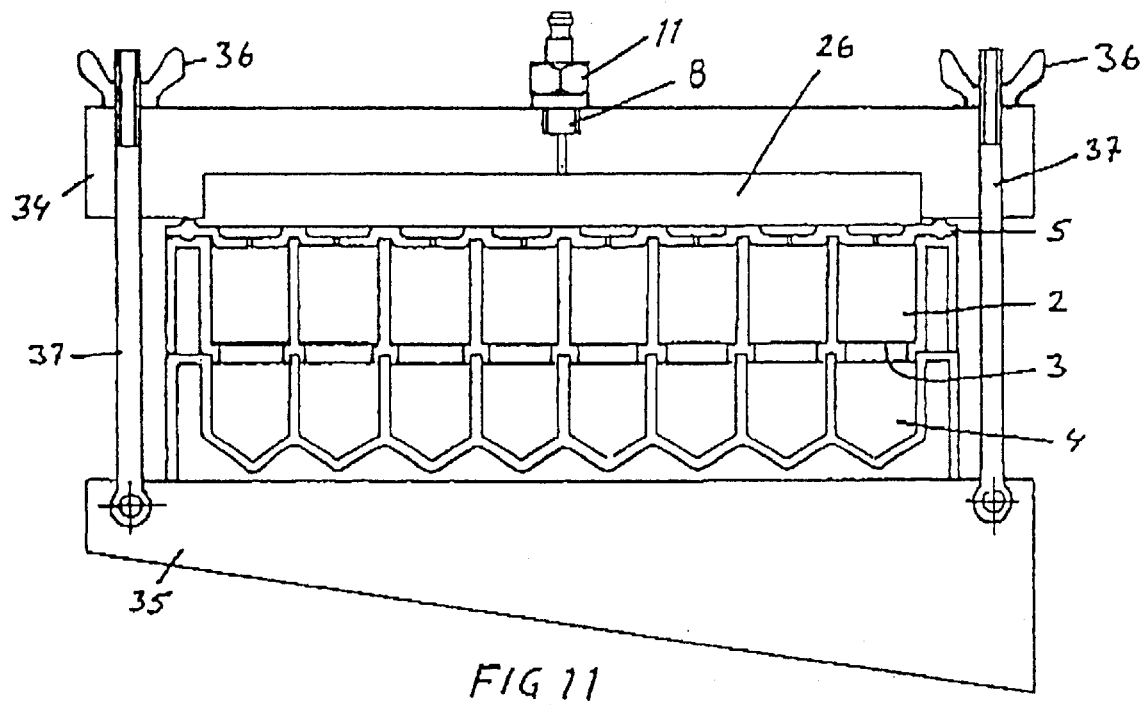
FIG. 11 shows a device according to the invention, partly in section, having a number of individual combinations of sample reservoir, filter means and filtrate container arranged in rows and columns provided with a common pressurized chamber.

In FIG. 11 a particular embodiment of the invention is illustrated. A number of individual combinations of a sample reservoir 2, a filter means 3 and a filtrate container 4 are arranged in rows and columns provided with a common pressurized chamber 26. Gas under pressure is entered in the chamber 26 through an inlet 8 provided with a check valve 11 as in the device according to FIG. 2, for example. A cap 5 of the same type as shown in e.g. FIG. 2 is preventing liquid sample from splashing up into the pressure reservoir or chamber 26 which could contaminate adjacent samples. A small slit in the cap for each sample reservoir is communicating the pressure to the respective reservoir. All devices will thus at any moment during the whole filtration procedure have the same pressure. The combinations of sample reservoirs, filter means and filtrate containers are pressed together between two pressure plates 34 and 35 by means of wing nuts 36 and tie rods 37. An integrated O-ring of the same type as shown in e.g. FIG. 2 seals the chamber 26 against the edge of the plate comprising the sample reservoirs.

In a particular embodiment the lower pressure plate is angled. This arrangement will create a tangential flow vector over the filter surface especially when the device is used in a centrifuge. This will help to keep the filter surface clean and thus the flow rate high. Retentate will mainly be collected along the edge of the sample reservoir to the left in FIG. 11. A dead stop can thus e.g. be arranged at that side the volume of which can be controlled by means of the angle of the lower pressure plate.

Figure 12:
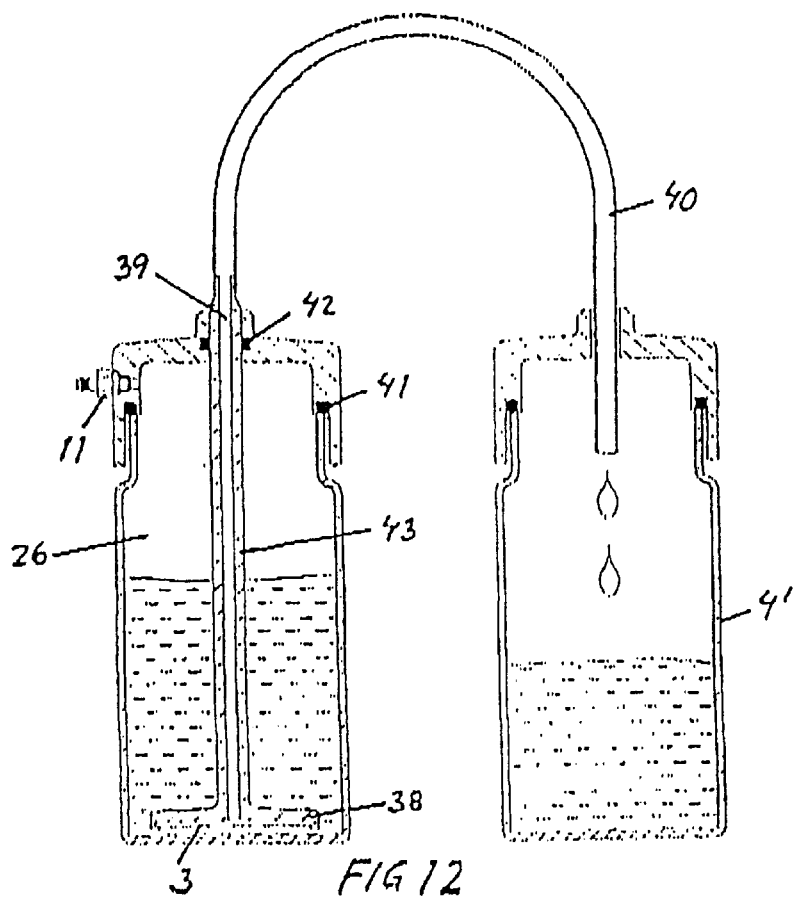
FIG. 12 shows partly in section a combination of a device according to the invention and a separate filtrate container.

In FIG. 12 another embodiment of the filtration cell is shown. The filter membrane is supported on the underside of a plate 38 which is arranged substantially horisontal at the lower part of the sample reservoir. The permeate side of the membrane is communicating through a substantially vertical filtrate duct 39 to the top and out of the device. Filtrate may be caused to permeate the membrane and exit the device through the filtrate duct 39.

The filtrate duct does not have to be arranged at the center of the plate 38 but could e.g. be arranged close to edge of the plate so that the duct follows the inner side wall of the sample reservoir. An inlet 8 provided with a check valve 11 is arranged in the cap to allow for the creation of an overpressure in the volume 26.

Figure 13:
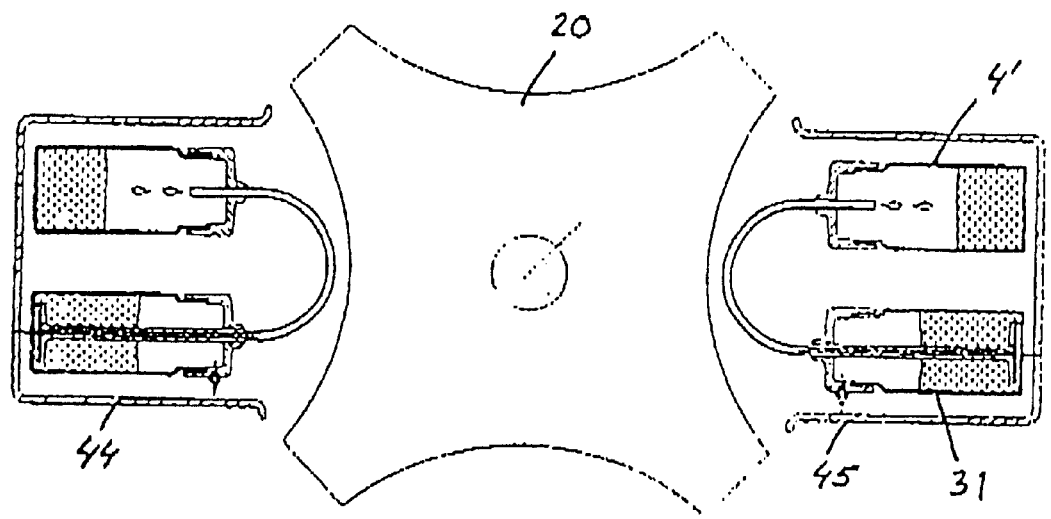
FIG. 13 shows the arrangement of two combinations according to FIG. 12 in two opposite buckets in a centrifuge.

Spinning such a device in a centrifuge will create a force vector on the macromolecules away from the membrane surface which will keep this surface clean. If no overpressure is present filtrate will raise in the duct until it reaches essentially the same level as in the sample reservoir. At this stage there will be no driving pressure difference left over the membrane and the filtration will stop. By adding an overpressure in the volume 26 it is however possible to create the necessary driving force to continue the filtration. Filtrate could e.g. be collected in a separate filtrate container 4', as shown in FIG. 12. In the embodiment shown in this figure air can escape from the filtrate container at the opening for the hose connecting the device with the container. Said container will be arranged in the same bucket on the centrifuge as shown in FIG. 13. The filtrate does of course not have to exit the device at the top of the same. The duct could e.g. be arranged to exit the filtrate through the sidewall of the sample reservoir.

The filtrate container 4' could also be arranged coaxially with the sample reservoir on the outside of the same in order to get a more compact design.

In the embodiment shown in FIG. 12 two O-rings 41 and 42 are sealing the top of the device. The O-ring 42 is allowing the tube 43 with the vertical duct 39 to slide axially in the outlet from the device. In order to prevent centrifugal forces to press the plate 38 against the bottom of the sample reservoir which would stop the filtration, distance elements, not shown, could be arranged at the bottom the sizes of which would also determine the dead stop for the device.

In general devices according to the above comprising the sample to be filtered can be pressurised as described in connection to e.g. FIG. 2 and can be used in different ways.

A device can e.g. be used as a free standing filtration unit (static filtration), it can be put in a centrifuge to be centrifuged at an appropriate speed (centrifugal filtration), cf. FIG. 9, or it can be put on a laboratory agitator (agitated filtration), cf. FIG. 10.

Static Filtration

The pressure difference between the sample reservoir and the filtrate container, due to under-pressure in the filtrate container or over-pressure in the sample reservoir, will force solvent and microsolute through the membrane(s) 3 which will then collect at the bottom of the filtrate container 4. The device may be left pressurised connected to its external air/gas source or be detached and placed in a different location such as a refrigerator to keep the sample cold if this is advantageous. In this case, pressurised gas contained above the sample in the sample reservoir and in the chamber 26 in the pressure resistant head portion 7 will provide sufficient accumulated pressure to complete the filtration process. Pressurised gas/air is entering the sample reservoir through the slit or hole 6 in the cap 5.

An additional advantage of the described device is that there are no tubing connections between the concentration chamber and the filtrate container. The bench space requirements are thus significantly reduced in relation to known devices. The elimination of tubing also reduces unrecoverable volume which is difficult to fully extract from the tube section.

Centrifugal filtration

In order to reduce problems related to the reduction of vector force as filtration progresses when using a centrifuge, the invention allows the combined effect of centrifugation and gas pressure to be used. The pressurised device containing the sample to be filtered is placed in a centrifuge and spun at an appropriate speed. Centrifugation will force solvent and molecules smaller than the porosity of the membrane through the membrane elements 3 and further through the filtrate ducts 24. The filtrate is collected at the bottom of the filtrate container 4. Centrifugal force, in addition to gas pressure related liquid pressure on the membrane, will sweep the solute across the membrane avoiding an excessive build up of molecules on the membrane surface. Macromolecules will collect at the bottom of the device away from the membrane surface. The accumulated gas pressure at the head of the device provides additional pressure on the membrane which is particularly useful when filtration has progressed to a point where the gravitational pressure of centrifugation is significantly reduced.

In FIG. 9 a centrifuge 20 is schematically shown in which two devices 31 of the described type have been placed diagonally. Two additional containers for compressed gas/air 32 each connected to a device 31 have been placed in adjacent buckets in a balanced configuration. This arrangement increases the capacity of pressurised gas/air. A pressure reservoir or a controllable constant pressure source may in an alternative be provided for in the centrifuge itself.

An advantage with this procedure is that there will be no build up of vacuum in the concentration chamber that could impede the filtration process as filtration progresses. Additionally the sample reservoir and the sample therein are completely sealed off from the external environment during the process which can be of importance when handling toxic or otherwise dangerous samples.

As indicated above the configuration according to FIG. 12 could be used in a centrifuge. This is illustrated in FIG. 13. The centrifuge 20 is shown schematically provided with only two buckets 44 and 45. The buckets are loaded in an appropriate way to get a good balance.

Agitated Filtration

Due to problems related to the accumulation of solutes on the membrane surface, filtration may be adversely affected during static filtration. The pressurised device may be placed on a suitable laboratory agitator, cf. FIG. 10, which will provide a shaking or orbital action to maintain residual solute in suspension by sweeping it away continuously from the membrane surface. With no spinning mechanism to create shear this is a much gentler process than stirred cell filtration. The cap 5 whose small slit(s) 6 remains normally closed impedes the solution from splashing out of the concentration chamber into the chamber 26 of the pressure resistant head portion and also blocks aerosols created in the sample reservoir to escape into the head portion which could cause contamination and reduced recovery of the final concentrate. To a certain degree this is also the case when the device is used in a centrifuge. In this process the pressure source may be kept attached or be disconnected as in the static filtration process.

FIGS. 4–6 show devices according to the invention in which an insert reservoir 12 has been inserted in the sample reservoir 2. The FIGS. 4A–6A show embodiments for use in pressurised mode and FIGS. 4B–6B show corresponding devices to be used without overpressure.

Figure 14:
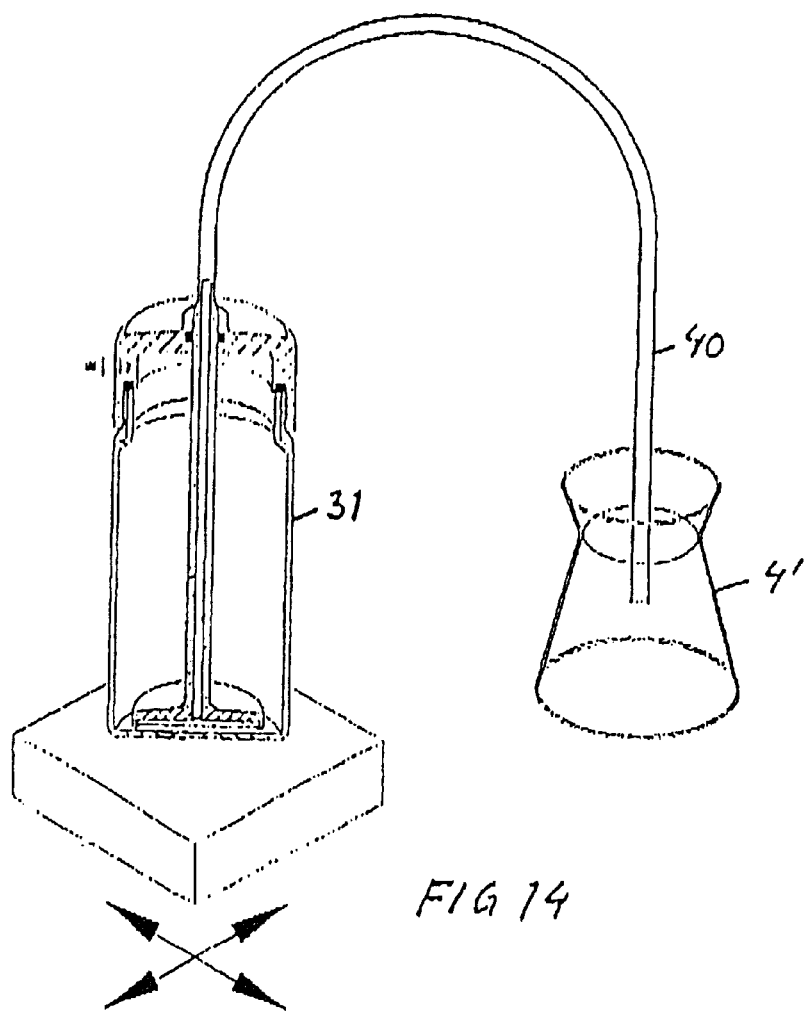
FIG. 14 shows partly in section a device according to the invention arranged on an agitator.

FIG. 14 shows a device as described in connection with FIG. 12 arranged on an agitator.

Sample washing

The devices according to FIGS. 4A and 4B are typically used for so called sample washing.

In order to clear a maximum of contaminating micromolecules for example salts through the membrane whilst retaining the macromolecules for example proteins several solute wash steps are frequently used in known methods. The sample is concentrated a first time and then a buffer solution is added and the diluted sample is then reconcentrated. This procedure is repeated several times until the contaminating microsolute is sufficiently reduced. A more efficient and time saving alternative is to continuously feed fresh buffer solution at the same speed as existing solute is cleared through the membrane. This method which is termed "constant volume diafiltration" requires significantly less solvent to achieve the same level of purification. The disadvantage of this method is that it requires a separate pressurised vessel filled with the buffer solution which is linked to the filtration chamber by a tube to feed buffer solution to the concentration chamber at the speed of filtration. This is cumbersome and requires additional investment in a pressure resistant tank and appropriate fittings.

Constant volume diafiltration can be much more easily carried out with a device according to the present invention, cf. FIGS. 3, 4A and 4B.

The sample is first concentrated in the concentration chamber 1 without insert reservoir e.g using the centrifugal or pressurised cell mode to a level below the shoulders 14 of the concentration chamber. This means that only the filtration chamber is still filled with sample liquid.

An inexpensive insert reservoir 12 is introduced into the sample reservoir 2 of the concentration chamber 1 which reservoir 12 is designed to fit snugly to the internal wall of the sample reservoir 12. A sealing means 17, e.g. in the form of an O-rig could be needed to secure the sealing.

Should an O-ring seal be used, this will suitably be fitted into a retaining groove 16 at the outer surface of the lower extremity of the insert reservoir. The inner wall of the sample reservoir 2 and/or the outer wall of the insert reservoir 12 are slightly conical so the insert reservoir will slide relatively easily in and out of the sample reservoir with the O-ring or alternative seal only fully engaging the wall of the sample reservoir towards the end of its permitted travel. The insert reservoir is retained from sliding too far into the sample reservoir by the shoulders 14 built into the bottom section of the sample reservoir, cf. FIG. 8, or by other means such as a flange 15 which will allow the insert reservoir to hang from the top of the sample reservoir. At least one small opening 13 of typically less than 3 mm is provided at the bottom of the insert reservoir.

Buffer solution is now added to the insert reservoir 12 and the assembled device is pressurised again. During e.g. centrifugation or pressurised cell filtration, buffer solution will enter the thin filtration channel 22 with the membrane or membranes 3 at the bottom of the concentration chamber 1 at the same speed as solvent and microsolutes are cleared through the membrane(s). The O-ring seal 17 on the filtrate container preventing solute mixing by pressure equilibration and the very small aperture 13 minimising any potential mixing caused by shaking. This method has proven to be much more efficient than repeated wash and concentration cycles and much simpler and less expensive than constant volume diafiltration using a separate reservoir.

Two stage filtration

Many biological solutions contain relatively large solids and suspended particles as well as very small micromolecules which need to be eliminated from the macromolecules of interest. Typically a first microfiltration step is often required to clarify and/or sterilise the sample before the further concentration of target molecules and the elimination of impurities.

In order to reduce the number of filtration steps required in sample processing, some known device holders can be stacked together to provide a double filtration during e.g. a centrifugal process. For example a solution may pass through a first relatively coarse microporous filter for clarification followed by the concentration of the molecules of interest by retaining them in an impermeable area on the edge of the second filter. Up until now this technique has been limited by the fact that the surfaces of stacked filters have been mounted in parallel to each other.

Two stage filtration can be much more efficiently carried out with the present invention than by means of devices and methods according to the known art.

The insert reservoir 12 as shown in FIGS. 5A, 5B is provided with a relatively high porosity membrane 18 fitted at the lower part of the reservoir. The membrane edge is sealed to the inner wall of the insert reservoir 12. A sealing method using e.g. heat, ultrasonic welding, interference fit or glue may be used. The central area of the membrane is supported by a ribbed channel structure, cf. FIGS. 7A, 7B that converges to an opening 13 so as to provide a filtrate passage to the filtration chamber 22. The insert reservoir is retained from sliding too far into the sample reservoir by the shoulders 14 built into the bottom section of the sample reservoir or by other means such as flanges 15 which will allow the insert reservoir to hang from the top of the sample reservoir as in the embodiment according to FIG. 4A.

FIG. 7A shows the same assembly as the one according to FIG. 5B in perspective view. When the lower portion of the insert container rests against the shoulder 14 and the side wall of the insert container bears against the inner wall of the concentration chamber a very good support for the insert container is assured. This means that a thinner and/or softer material can be used for this container. A softer more flexible material in the insert container makes it possible to arrange the sealing without e.g. an O-ring. The sealing could for instance be realized by means of a somewhat diverging skirt along the edge forming an integral part of the lower portion of the insert container 12.

In the procedure according to the invention, an insert reservoir 12 according to the above is introduced into the sample reservoir 2. This means that a configuration is achieved having the first coarse filter ideally positioned at 90 degrees to the axis of the device and the vector force with the objective to efficiently clear a maximum of the solute of interest through that filter. The second filter is arranged as described above with an angle to the vector force to avoid the build up of solute on the surface of this tighter filter.

In a method according to the invention making use of a device according to FIG. 5A the sample to be processed is filled into the insert reservoir 12 and the assembled device is pressurised. Alternatively a vacuum could of course be arranged in the filtrate container. The device can then be used as a free standing unit or be run in a centrifuge or on a laboratory agitator like the other devices according to the invention.

In the first filtration cup, large unwanted particles or macromolecules will be retained by the membrane whilst free passage will be available to the solvent and/or smaller macromolecules. This is essentially a sieving process that binds unwanted particles on the membrane but retains a minimum amount of smaller molecules. Once through the first membrane the solution passes into the filtration chamber 22 whose membrane is mounted at a minimum of 45 degrees to the coarser membrane upstream. In this method, macromolecules, which are larger than the porosity of the second membrane, now sweep the second membrane surface and are collected in a concentrate pocket 31 situated on the bottom of the filtration chamber, whilst the solvent and smaller micromolecules have free passage through the second membrane and are collected in the filtrate container 4.

This method provides improved recovery of the macromolecules of interest in relation to methods making use of sequential horizontal or vertical filters because it gives minimum solute retention on the first membrane and a good sweeping action and easy concentrate recovery at the second membrane.

A particular advantage of this assembly when used in a gas pressurised agitated mode is that the shaking or vortex action will maintain the solute in suspension in both the insert reservoir and in the filtration chamber, improving the speed of filtration through both membranes.

This type of insert reservoir may also be used for one stage filtration by arranging it directly on a filtrate container, cf. FIG. 7B. In this arrangement it can be used directly in a centrifuge. With the additional attachment of the pressure resistant head portion 7 it can also be used in pressurised mode. The whole assembly may be agitated by mounting it on a laboratory shaker or agitator. This arrangement is particularly useful when the solute of interest is the filtrate for example when removing bacteria from a solution and the objective is to recover a maximum amount of solute in the filtrate.

Combined solid phase extraction and concentration

In the purification of biological solutions, when it is required to separate macromolecules of similar size filtration methods are usually not appropriate. For this purpose, macromolecules are often passed through a resin bed that will bind macromolecules on the basis of their respective physical and chemical characteristics. For example, cation or anion exchange resins can be used to bind any given protein but allow free passage to other proteins with a different charge. In this manner, the protein of interest is first retained by the gel whilst contaminants are eluted and then by correcting the pH in a new buffer solution, the target protein can then be eluted off separately. This type of procedure is frequently called Solid Phase Extraction.

The use of the device according to the invention in this procedure allows more control of the elution speed and can additionally be used for protein concentration and buffer exchange.

The insert reservoir 12 as shown in FIGS. 6A, 6B which is of the same general type as in FIGS. 4A, 4B is packed with a suitable resin bed 19 at the lower part of the reservoir. The resin is sandwiched between two porous sinters or membranes 32 for containment of the resin and to provide a homogeneous bed.

In the procedure according to the invention, an insert reservoir 12 according to the above is introduced into the sample reservoir 2.

A buffer solution is filled into the insert reservoir and the assembled device is first pressurised to equilibrate the gel bed or column and the filtration chamber.

Remaining buffer solution is emptied from the insert reservoir and is replaced by the solution to be purified. Under e.g. gas or centrifugal pressure the solution will permeate through the gel bed with the flow greatly reduced mainly by the back pressure created by the membrane element in the filtration chamber. The speed of flow through the gel bed can be further optimised by the choice of membrane porosities and pressure combinations. Macromolecules with an affinity to the resin will bind strongly whilst others will pass through the resin bed into the filtration chamber where they will be concentrated. Micromolecules and solvent will be filtered through the membrane 3 and will be collected in the filtrate container 4.

The insert reservoir now containing the fraction of interest is moved into a new concentration chamber and the insert reservoir is filled with a modified buffer solution capable of eluting the target molecule. The assembly is again pressurised so as to elute and concentrate the target molecule.

Should it be required, a washing step may then be carried out with a device according to the invention to exchange the buffer solution that has been used to elute the target molecules, for example in order to return the solution to a physiological pH.

Test results

Laboratory experiments have been made in order to evaluate the filtration performance of an embodiment of the filtration cell according to the invention. The same filtration cell, Vivaspin 15, produce No. VS 1511, manufactured by the company Vivascience Ltd., has been set up to run in the alternative ways according to the invention. Thus, filtration cells of 15 ml total capacity fitted with a membrane of 5000 molecular weight cut off were filled with 10 ml of a solution containing 1 mg/ml of BSA. The cells were run alternatively using 6 bar pressure with no further equipment, 6 bar pressure combined with agitation on a laboratory shaker, 3000G centrifugation with no pressure, 500 G centrifugation combined with 6 bar initial pressure and finally 3000 G centrifugation combined with 6 bar initial pressure. All tests were run in duplicate and the following table shows the average of the two runs.

It can be seen that the filtration cell will concentrate the solution approximately 50 times under all conditions but that the time required will vary according to conditions and equipment used. The slowest performance was observed using the pressurised filtration cell with no agitation to stop the accumulation of solute on the membrane surface. The time required was more than halved when pressure was combined with agitation. The greatest speed was observed when the filtration cell was used in a centrifuge in combination with gas pressure.

The test shows that the filtration cell easily adapts itself to the availability of laboratory equipment and demonstrates the superior performance of the cell when gas pressure is combined with a laboratory shaker or centrifuge.

| | VIVASPIN 15 ALTERNATIVE PROCESSING COMPARISONS 10 ML START VOLUME (BSA 1.0 MG/ML) | | | | | | | | | |
|---|---|---|---|---|---|---|---|---|---|---|
| | STATIC WITH PRESS 6 BAR | | PRESS & SHAKE 6 BAR, SHAKE 3 | | CENTRIFUGE ONLY 3,000 g | | PRESS. & CENTRIF. 6 BAR, 500 g | | PRESS. & CENTRIF. 6 BAR, 3,000 g | |
| | ML CUM. | ML PART | ML CUM. | ML PART | ML CUM. | ML PART | ML CUM. | ML PART | ML CUM. | ML PART |
| TIME MIN. | | | | | | | | | | |
| 5 | 1.436 | 1.438 | 2.490 | 2.490 | 4.823 | 4.823 | 4.010 | 4.010 | 6.140 | 6.140 |
| 10 | 2.283 | 0.845 | 4.450 | 1.960 | 6.630 | 3.807 | 7.443 | 3.433 | 9.503 | 3.363 |
| 15 | | | 7.000 | 2.550 | 9.440 | 0.810 | 8.858 | 1.415 | 9.828 | 0.325 |
| 20 | 3.888 | 1.605 | 8.390 | 1.390 | 9.693 | 0.253 | 9.765 | 0.907 | | |
| 25 | | | 9.530 | 1.140 | 9.795 | 0.102 | 9.858 | 0.093 | | |
| 30 | 5.203 | 1.315 | 9.805 | 0.075 | | | | | | |
| 35 | | | 9.700 | 0.095 | | | | | | |

-continued

| | VIVASPIN 15 ALTERNATIVE PROCESSING COMPARISONS 10 ML START VOLUME (BSA 1.0 MG/ML) | | | | | | | | |
|---|---|---|---|---|---|---|---|---|---|
| | STATIC WITH PRESS 6 BAR | | PRESS & SHAKE 6 BAR, SHAKE 3 | | CENTRIFUGE ONLY 3,000 g | | PRESS. & CENTRIF. 6 BAR, 500 g | | PRESS. & CENTRIF. 6 BAR, 3,000 g | |
| | ML CUM. | ML PART | ML CUM. | ML PART | ML CUM. | ML PART | ML CUM. | ML PART | ML CUM. | ML PART |
| 40 | 6.800 | 1.597 | 9.760 | 0.060 | | | | | | |
| 50 | 8.220 | 1.420 | | | | | | | | |
| 60 | 9.330 | 1.110 | | | | | | | | |
| 70 | 9.660 | 0.330 | | | | | | | | |
| 50 | 9.730 | 0.010 | | | | | | | | |
| 90 | 9.750 | 0.020 | | | | | | | | |

What is claimed is:

1. Device for concentrating and/or purifying macromolecules in a solution comprising a concentration chamber (1) including a sample reservoir (2) for the liquid sample to be processed and filter means (3) for filtering said liquid sample, and a filtrate container (4) for collecting the filtrate characterized in that said sample reservoir (2) is provided with an insert reservoir (12) having at least one one-way opening (13) for the liquid sample at its lower portion through which liquid is fed to the volume adjacent the filter means (3) and the liquid is prevented from returning to the insert reservoir.

2. Device according to claim 1 characterized in that said insert reservoir (12) is provided at its lower portion with a microporous filter arrangement (18) for filtering the liquid sample leaving the reservoir (12) through the opening (13).

3. Device for concentrating and/or purifying macromolecules in a solution comprising a concentration chamber (1) including a sample reservoir (2) for the liquid sample to be processed and filter means (3) for filtering said liquid sample, and a filtrate container (4) for collecting the filtrate characterized in that said sample reservoir (2) is provided with an insert reservoir (12) having at least one one-way opening (13) for the liquid sample at its lower portion through which liquid is fed to the volume adjacent the filter means (3) and the liquid is prevented from returning to the insert reservoir, said insert reservoir (12) is provided at its lower portion with a microporous filter arrangement (18) for filtering the liquid sample leaving the reservoir (12) through the opening (13), and said insert reservoir (12) is provided at its lower portion with a gel bed (19) for processing the liquid sample leaving the reservoir (12) through the opening (13).

4. Device for concentrating and/or purifying macromolecules in a solution comprising a concentration chamber (1) including a sample reservoir (2) for the liquid sample to be processed and filter means (3) for filtering said liquid sample, and a filtrate container (4) for collecting the filtrate characterized in that it further comprises an arrangement in the form of a pressure resistant head portion (7) provided with a chamber (26) for accumulating gas under pressure having an inlet (8) for the gas under pressure, fixed in gas tight relation to and communicating with said sample reservoir for creating and maintaining a gas pressure related pressure difference across said filter means (3) and a sealing cap (5) closing said sample reservoir (2) provided with at least one opening (6) in the form of a slit (6) or small hole letting gas through in one direction and blocking aerosol or splashing liquid in the opposite direction separating said sample reservoir (2) from said pressure resistant head portion (7) and is providing said gas tight relation around its edge between said head portion (7) and said sample reservoir (2), and in that said arrangement has the form of gas tight sealing arrangement (9) between said filtrate container (4) and the environment and an outlet (10) for gas from said filtrate container (4) for evacuating said container.

5. Device according to claim 4 characterized in that said inlet (8) is provided with a check valve (11).

6. Device according to claim 4 characterized in that said outlet (10) is provided with a check valve.

7. Device for concentrating and/or purifying macromolecules in a solution comprising a concentration chamber (1) including a sample reservoir (2) for the liquid sample to be processed and filter means (3) for filtering said liquid sample, and a filtrate container (4) for collecting the filtrate characterized in that said sample reservoir (2) is provided with an insert reservoir (12) having at least one one-way opening (13) for the liquid sample at its lower portion through which liquid is fed to the volume adjacent the filter means (3) and the liquid is prevented from returning to the insert reservoir, and in that the outer surface of said insert reservoir (12) as well as the inner surface of said sample reservoir (2) both are slightly conical to facilitate the insertion.

8. Device according to claim 7 characterized in that the outer surface of said insert reservoir (12) at its lower portion is provided with a groove (16) comprising a gas tight sealing means (17) for separating the volume adjacent the filter means (3) from the rest of the sample reservoir (2).

9. Device for concentrating and/or purifying macromolecules in a solution comprising a concentration chamber (12) including a sample reservoir (2) for the liquid sample to be processed and filter means (3) for filtering said liquid sample, and a filtrate container (4) for collecting the filtrate characterized in that it further comprises an arrangement for creating and maintaining a gas pressure related pressure difference across said filter means (3), and that said sample reservoir (2) is provided with an insert reservoir (12) having at least one opening (13) for the liquid sample at its lower portion through which liquid is fed to the volume adjacent the filter means (3), and that said insert reservoir (12) is provided at its lower portion above said opening with a microporous filter arrangement (18) for filtering the liquid sample leaving the insert reservoir (12) through the opening (13).

10. Device for concentrating and/or purifying macromolecules in a solution comprising a concentration chamber (1) including a sample reservoir (2) for the liquid sample to be processed and filter means (3) for filtering said liquid sample, and a filtrate container (4) for collecting the filtrate characterized in that it further comprises an arrangement for creating and maintaining a gas pressure related pressure difference across said filter means (3), and that said sample reservoir (2) is provided with an insert reservoir (12) having at least one opening (13) for the liquid sample at its lower portion through which liquid is fed to the volume adjacent the filter means (3), and that said insert reservoir (12) is provided at its lower portion above said opening with a gel bed (19) for processing the liquid sample leaving the insert reservoir (12) through the opening (13).

11. Apparatus for concentrating and/or purifying macromolecules in a solution including a centrifuge (20) for spinning devices and said devices, each of said devices comprising:

a concentration chamber (1) including a sample reservoir (2) for the liquid sample to be processed and filter means (3) for filtering said liquid sample, and a filtrate container (4) for collecting the filtrate, wherein said devices each are provided with an arrangement for creating and maintaining a gas pressure related pressure difference across said filter means (3).

12. Apparatus for concentrating and/or purifying macromolecules in a solution including a centrifuge for spinning devices and said devise, each of said devices comprising:

a concentration chamber (1) including a sample reservoir (2) for the liquid sample to be processed and filter means (3) for filtering said liquid sample, and a filtrate container (4) for collecting the filtrate, wherein said sample reservoir (2) is provided with an insert reservoir (12) having at least one opening (13) for the liquid sample at its lower portion through which liquid is fed to the volume adjacent the filter means (3), and said insert reservoir (12) is provided at its lower portion with a microporous filter arrangement (18) for filtering the liquid sample leaving the reservoir (12) through the opening (13).

13. Apparatus for concentrating and/or purifying macromolecules in a solution including at least one concentrating and/or purifying device and said devices, each of said devices comprising:

a concentration chamber (1) including a sample reservoir (2) for a liquid sample to be processed and filter means (3) for filtering said liquid sample, and a filtrate container (4) for collecting the filtrate, wherein each device is arranged on a mechanism for providing an orbital or oscillating movement, and each device is provided with an arrangement for creating and maintaining a gas pressure related pressure difference across said filter means (3).

14. Apparatus according to claim 13 characterized in that said arrangement has the form of a pressure resistant head portion (7) provided with a chamber (26) for accumulating gas under pressure having an inlet (8) for the gas under pressure, fixed in gas tight relation to and communicating with said sample reservoir.

15. Apparatus for concentrating and/or purifying macromolecules in a solution including a centrifuge (20) for spinning devices and said devices, each of said devices comprising:

a concentration chamber (1) including a sample reservoir (2) for the liquid sample to be processed and filter means (3) for filtering said liquid sample, and a filtrate container (4) for collecting the filtrate, wherein said devices each are provided with an arrangement for creating and maintaining a gas pressure related pressure difference across said filter means (3), and a sealing cap (5) is arranged separating said sample reservoir (2) from said pressure resistant head portion (7) and is providing said gas tight relation around its edge between said head portion (7) and said sample reservoir (2), said sealing cap (5) being provided with at least one opening (6) in the form of a slit (6) or small hole letting gas through in one direction and blocking aerosols and splashing liquid in the opposite direction.

16. Method for concentrating and/or purifying macromolecules in a liquid solution making use of a centrifuge (20) for spinning a number of devices, each of the devices comprising a concentration chamber (1) including a sample reservoir (2) for a liquid sample to be processed and filter means (3) for filtering said liquid sample, and a filtrate container (4) for collecting the filtrate, comprising the steps of:

filling said liquid solution into said sample reservoirs (2), putting into each sample reservoir (2) its corresponding filtrate container (4), providing a pressure resistant head portion )7) with a chamber (26) for accumulating gas under pressure having an inlet (8) for the gas under pressure, and fixing in gas tight relation the head portion on top of and communicating with each sample reservoir (2), pressurizing each such assembled device from a source of pressurized gas, spinning said devices in a balanced configuration in said centrifuge at an appropriate speed, whereby the accumulated gas pressure at the head of the device provides additional driving force for the filtration at the end of the filtration process when the centrifugal forces have significantly decreased.

17. Method according to claim 16 characterized in that at least two separate pressure sources are put in said centrifuge in a balanced configuration and are each connected to one of said devices to provide gas under pressure during the spinning operation of the centrifuge.

18. Method for concentrating and/or purifying macromolecules in a liquid solution making use of at least one concentrating and/or purifying device comprising a concentration chamber (1) including a sample reservoir (2) for a liquid sample to be processed and filter means (3) for filtering said liquid sample, and a filtrate container (4) for collecting the filtrate, comprising the steps of:

concentrating said liquid sample in said concentration chamber to a certain remaining volume, introducing into said sample reservoir an insert reservoir (12) having at least one opening (13) at its lower portion through which liquid could be fed to said remaining volume and sealing the insert to the inner wall of said sample reservoir (2), filling a buffer solution into said insert reservoir, providing said at least one device with an arrangement for creating and maintaining a gas pressure related pressure difference across said filter means (3), arranging said at least one device on a mechanism for providing an orbital or oscillating movement to said at least one device and activating said mechanism so that buffer solution enters said remaining volume of liquid sample at the same speed as solvent and microsolutes are cleared through the filter means (3).

19. Method for concentrating and/or purifying macromolecules in a liquid solution making use of at least one concentrating and/or purifying device comprising a concentration chamber (1) including a sample reservoir (2) for a liquid sample to be processed and filter means (3) for filtering said liquid sample, and a filtrate container (4) for collecting the filtrate, comprising the steps of:

introducing an insert reservoir (12) having at least one opening (13) at its lower portion through which liquid could be fed to a volume of the concentration chamber below said insert reservoir and which at its lower portion above said opening is provided with a microporous filter arrangement (18) into the sample reservoir (2) of the concentration chamber (1), filling said liquid sample into said insert reservoir, providing said at least one device with an arrangement for creating and maintaining a gas pressure related pressure difference across said filter means (3), arranging said at least one device on a mechanism for providing an orbital or oscillating movement to said at least one device and activating said mechanism so that during the filtering process large unwanted particles and macromolecules will be retained by the filter arrangement (18) and the macromolecules of interest will be retained by filter means (3).

20. Method for separating macromolecules in a liquid solution making use of a centrifuge (20) for spinning a number of devices each comprising a concentration chamber (1) including a sample reservoir (2) for a liquid sample to be processed and filter means (3) for filtering said liquid sample, and a filtrate container (4) for collecting the filtrate comprising the steps of:

introducing an insert reservoir (12) having at least one opening (13) at its lower portion through which liquid could be fed to a volume of the concentration chamber below said insert reservoir and which at its lower portion above said opening is provided with a bed of a resin (19) which can bind macromolecules on the basis of their respective physical and chemical characteristics into the sample reservoir (2) of the concentration chamber (1), filling a buffer solution into the insert reservoir (12) and causing the buffer solution to penetrate the resin bed and fill up the volume between the filter means (3) and the at least one opening (13), emptying the remaining buffer solution from the insert reservoir, filling the liquid sample to be processed into the insert reservoir, putting said devices in a balanced configuration in said centrifuge and spinning at an appropriate speed, whereby the solution will permeate through the gel bed witg a flow rate reduced by the back pressure created by the filter means (3), macromolecules with an affinity to the resin will bind strongly in said resin whilst others will pass through the resin bed into the volume of the concentration chamber adjacent the filter means (3) where they will be concentrated.

21. Method for concentrating and/or purifying macromolecules in a liquid solution making use of a centrifuge (20) for spinning a number of devices each comprising a concentration chamber (1) including a sample reservoir (2) for a liquid sample to be processed and filter means (3) for filtering said liquid sample, and a filtrate container (4) for collecting the filtrate comprising the steps of:

filling said liquid solution into said sample reservoirs (2), putting each sample reservoir (2) in its corresponding filtrate container (4), fixing a pressure resistant head portion (7) provided with a chamber (26) for accumulating gas under pressure having an inlet (8) for the gas under pressure, in gas tight relation on top of and communicating with each sample reservoir (2), pressurizing each such assembled device from a source of pressurize gas, putting said devices in a balanced configuration in said centrifuge and spinning at an appropriate speed, whereby the accumulated gas pressure at the head of the device provides additional driving force for the filtration which will speed up the filtration especially at the end of the filtration process when the centrifugal forces have significantly decreased.

\* \* \* \* \*